United States Patent
McGhie

(10) Patent No.: US 10,092,276 B2
(45) Date of Patent: Oct. 9, 2018

(54) TISSUE ACQUISITION DEVICE WITH INDICATION SYSTEM

(71) Applicant: Cook Medical Technologies LLC, Bloomington, IN (US)

(72) Inventor: Thomas W. McGhie, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 342 days.

(21) Appl. No.: 14/211,595

(22) Filed: Mar. 14, 2014

(65) Prior Publication Data

US 2014/0276208 A1  Sep. 18, 2014

Related U.S. Application Data

(60) Provisional application No. 61/789,924, filed on Mar. 15, 2013.

(51) Int. Cl.
*A61B 10/02* (2006.01)

(52) U.S. Cl.
CPC .............................. *A61B 10/0275* (2013.01)

(58) Field of Classification Search
CPC ............ A61B 10/0233; A61B 10/0266; A61B 10/0275; A61B 10/0283; A61B 2090/0811; A61M 2025/0004–2025/0006
See application file for complete search history.

(56) References Cited

U.S. PATENT DOCUMENTS

| | | |
|---|---|---|
| 3,995,619 A | 12/1976 | Glatzer |
| 4,600,014 A | 7/1986 | Beraha |
| 5,031,634 A | 7/1991 | Simon |
| 5,156,160 A | 10/1992 | Bennett |
| 5,172,702 A | 12/1992 | Leigh et al. |
| 5,195,533 A | 3/1993 | Chin et al. |
| 5,313,958 A | 5/1994 | Bauer |
| 5,335,672 A | 8/1994 | Bennett |
| 5,810,744 A | 9/1998 | Chu et al. |
| 5,916,175 A | 6/1999 | Bauer |
| 5,989,196 A | 11/1999 | Chu et al. |
| 6,165,136 A | 12/2000 | Nishtala |
| 6,203,925 B1 | 3/2001 | Attard et al. |
| 6,283,925 B1 * | 9/2001 | Terwilliger ........ A61B 10/0233 600/562 |
| 6,749,576 B2 * | 6/2004 | Bauer ................ A61B 10/0275 600/564 |

(Continued)

FOREIGN PATENT DOCUMENTS

WO  WO 2011121328 A2 * 10/2011 ............. A24D 3/041

*Primary Examiner* — Michael C Stout
(74) *Attorney, Agent, or Firm* — Woodard, Emhardt, Moriarty, McNett & Henry LLP

(57) ABSTRACT

Among other things, there is disclosed a biopsy needle system in which the needle is capable of obtaining more than one length of sample. Generally, the needle includes an inner stylet, an outer cannula, and a handle connected to the stylet and cannula. The stylet has a notch that is extendable from the cannula to accommodate a tissue sample. An insert member is provided for attachment to the handle to make the amount of exposed notch smaller. Consequently, when the insert member is not attached to the handle, the needle can obtain a larger sample of tissue, and when the insert member is attached to the handle, the needle can obtain a smaller sample of tissue.

12 Claims, 6 Drawing Sheets

(56) References Cited

U.S. PATENT DOCUMENTS

| | | |
|---|---|---|
| 7,481,775 B2 | 1/2009 | Weikel, Jr. et al. |
| 7,517,322 B2 | 4/2009 | Weikel et al. |
| 7,717,861 B2 | 5/2010 | Weikel et al. |
| 7,730,608 B2 | 6/2010 | Kvalheim |
| 7,766,843 B2 | 8/2010 | Voegele |
| 7,846,109 B2 | 12/2010 | Parihar et al. |
| 7,862,518 B2 | 1/2011 | Parihar |
| 8,043,316 B2 | 10/2011 | Hardin |
| 8,096,773 B2 | 1/2012 | Chang |
| 8,187,203 B2 | 5/2012 | McClellan |
| 8,197,419 B2 * | 6/2012 | Field ............... A61B 10/0275 600/567 |
| 8,343,072 B2 | 1/2013 | Bacon et al. |
| 8,506,504 B2 | 8/2013 | Field et al. |
| 8,728,005 B2 | 5/2014 | McClellan |
| 8,734,363 B2 | 5/2014 | Bacon |
| 8,740,811 B2 | 6/2014 | Fortems et al. |
| 2003/0163062 A1 * | 8/2003 | Bauer ............... A61B 10/0275 600/567 |
| 2004/0153003 A1 | 8/2004 | Cicenas et al. |
| 2004/0167434 A1 | 8/2004 | Fisher |
| 2004/0186393 A1 * | 9/2004 | Leigh ............... A61B 10/0266 600/567 |
| 2005/0075580 A1 * | 4/2005 | Leigh ............... A61B 10/0266 600/567 |
| 2006/0200041 A1 | 9/2006 | Weikel et al. |
| 2006/0200042 A1 | 9/2006 | Weikel et al. |
| 2006/0271082 A1 * | 11/2006 | Kirchhevel ...... A61B 17/32002 606/170 |
| 2007/0208272 A1 | 9/2007 | Voegele |
| 2007/0255170 A1 | 11/2007 | Hibner et al. |
| 2008/0287825 A1 * | 11/2008 | Cooke ............... A61B 10/0275 600/562 |
| 2009/0112119 A1 * | 4/2009 | Kim ................... A61B 10/0275 600/564 |
| 2009/0299220 A1 * | 12/2009 | Field ................. A61B 10/0275 600/567 |
| 2009/0299221 A1 * | 12/2009 | Bacon ............... A61B 10/0275 600/567 |
| 2010/0312141 A1 | 12/2010 | Keast et al. |
| 2011/0190660 A1 | 8/2011 | Levy |
| 2012/0179065 A1 * | 7/2012 | Ferree ............... A61B 10/0275 600/567 |
| 2012/0253230 A1 | 10/2012 | Williams et al. |

* cited by examiner

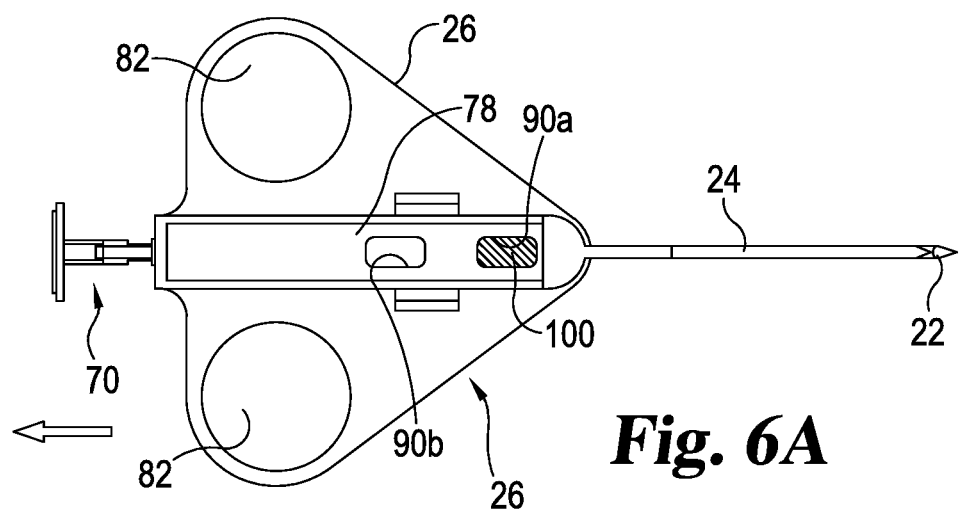
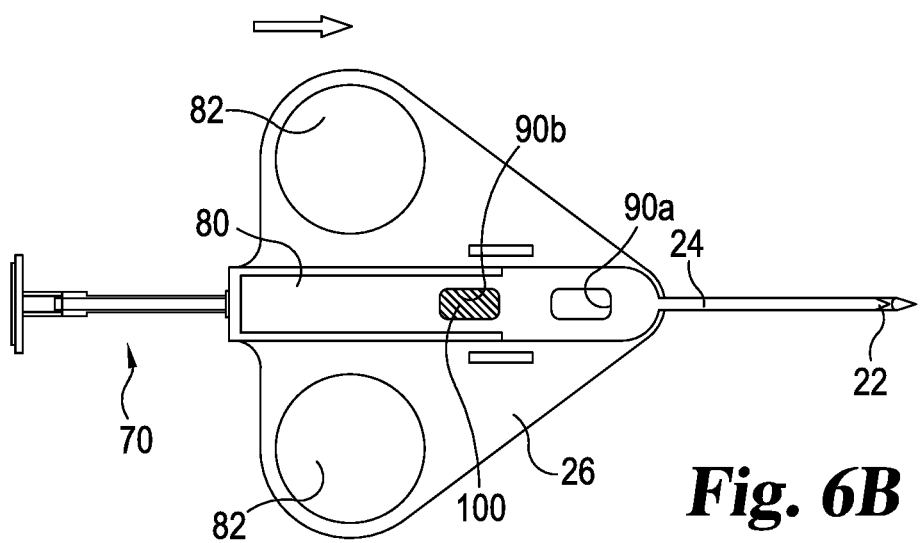

TISSUE ACQUISITION DEVICE WITH INDICATION SYSTEM

This application claims the benefit of U.S. Provisional Application Ser. No. 61/789,924, filed on Mar. 15, 2013, which is incorporated herein by reference in its entirety.

The present disclosure concerns devices such as biopsy needles for obtaining a sample of human or animal tissue for testing or study. In particular, it concerns tissue-obtaining devices that allow a user to easily assure that the device is correctly set for use even after user has begun.

BACKGROUND

A variety of biopsy needles and similar devices for obtaining a tissue sample from a patient are known. Commonly, such devices include a thin needle or stylet that can be inserted into the skin of the patient near the location of tissue to be sampled, such as suspected malignancies or other tissue of interest. Once the distal end or other cutting portion of the needle or stylet is within the tissue of interest, a portion of the tissue is excised and captured. The needle or stylet is withdrawn with the tissue sample, which can be retrieved from the device and studied.

Such products have proven quite effective in obtaining tissue in a minimally-invasive manner and with minimal discomfort to the patient. Their lightweight nature, combined with their ease of operation and reusability, make them excellent for sampling tissue that may present or indicate a health problem to the patient.

Biopsy needles designed to obtain samples of a fixed length are familiar, and in many cases that setting is either for a length of sample of 10 mm or 20 mm. Biopsy needles or other tissue sampling devices have been proposed that permit a variation of sample size, as by allowing the user to select or set the throw length to particular discrete settings for example. It can occur that the user forgets the setting he or she has chosen, or whether he or she has properly cocked or set the device for taking a sample at all. Further, the user may wish to reconfirm the setting as a part of his or her best practices. There remains a need for tissue sampling devices capable of obtaining varying amounts of tissue depending on a particular situation, and which permits easy confirmation that the device is set for a desired sample size.

SUMMARY

Among other things, there is disclosed tissue sample acquisition devices, such as biopsy needles, that include a handle and a sampling portion. In particular embodiments, the handle has an upper surface adapted to generally face a user during use of the device, and which has first and second openings. The sampling portion has a slide member adapted to slide with respect to the upper surface of the handle, an elongated needle at least partially extending from the handle, and a hub connecting the needle and the slide member. The sampling portion includes at least one visually contrasting portion, having an immediately observable visual contrast with one or more adjacent parts of the sampling portion and with the handle. At least part of the sampling portion and the handle are movable with respect to each other between at least a first relative configuration (corresponding to an unarmed state, e.g. not ready for firing) and a second relative configuration (corresponding to an armed state, e.g. ready for firing). When the sampling portion and handle are in the first relative configuration, at least part of the at least one visually contrasting portion is visible through the first opening, and when the sampling portion and handle are in the second relative configuration, at least part of the at least one visually contrasting portion is visible through the second opening.

Certain embodiments place the at least one visually contrasting portion as at least part of the slide member, and/or as at least part of the hub. The hub may be a part fitted into the slide member, the slide member being of substantially the same color as the handle, and the hub at least partially of a color visually contrasting with the slide member. As particular examples, the hub or other visually contrasting portion may be of a solid color that is easily contrasted with the general color of the handle. Where the cannula is partially within the handle and emerges from the handle at a particular location, the first opening may be closer to that particular location than is the second opening. The handle's longitudinal axis (e.g. an axis generally parallel to a portion of the elongated needle adjacent to or within the handle) may be generally parallel to a line connecting the first and second openings. Alternatively, the first opening can be laterally offset to a first side of the longitudinal axis and the second opening laterally offset to a second side of the longitudinal axis, so that when the upper surface of the handle is observed, the longitudinal axis is between and not intersecting the first and second openings. The sampling portion can have multiple visually contrasting portions, for example first and second such portions, and in the first relative configuration a first visually contrasting portion is visible through the first opening, and in the second relative configuration a second visually contrasting portion is visible through the second opening. Such multiple visually contrasting portions can include different colors. The first relative configuration may be a relative position between the slide member and the upper surface of the handle wherein the slide member is held at rest relative to the surface, and the second relative configuration is a relative position between the slide member and the surface wherein the slide member has been retracted from the first relative configuration and is held at rest relative to the surface.

In other embodiments, a biopsy needle or other tissue sample acquisition device includes a handle that has a surface with first and second openings. A sampling portion has an elongated cannula that at least partially extends from the handle connected to a slide member adapted to slide with respect to the surface. The sampling portion has at least one visually contrasting portion, the at least one visually contrasting portion having an immediately observable visual contrast with one or more adjacent parts of the handle. At least part of the sampling portion and the handle are movable with respect to each other between at least a first relative configuration and a second relative configuration. The first relative configuration corresponds to a first armed state operationally adapted to result in obtaining a first sample size, and the second relative configuration corresponds to a second armed state operationally adapted to result in obtaining a second sample size different from the first sample size. When the sampling portion and handle are in the first relative configuration, at least part of the at least one visually contrasting portion is visible through the first opening. When the sampling portion and handle are in the second relative configuration, at least part of the at least one visually contrasting portion is visible through the second opening.

The slide member can include, in particular embodiments, first and second visually contrasting portions and a longitudinal axis, with the first and second visually contrasting portions offset from each other longitudinally and offset laterally from and on respective sides of the longitudinal axis. In the noted first relative configuration, the first visually contrasting portion is visible through the first opening, and in the second relative configuration, the second visually contrasting portion is visible through the second opening. The at least one visually contrasting portion is at least part of a hub of the cannula in certain embodiments, and in others may be part(s) of the slide member. Embodiments are disclosed in which, in the first relative configuration, a different view is visible through the second opening, the different view including one of (a) a part of the sampling portion visually similar to an area adjacent the second opening and (b) empty space. Similarly, in the second relative configuration, a different view may be visible through the first opening, the different view comprising one of (a) a part of the sampling portion visually similar to an area adjacent the second opening and (b) empty space.

Embodiments of a tissue sample acquisition device (e.g. biopsy needle) that include a handle with a first observation area and a second observation area and a sampling portion including an elongated member are disclosed. The sampling portion and the handle have at least a first relative configuration and a second relative configuration. The first relative configuration corresponds to an operative state that is either unarmed or armed to enable the sampling portion to capture a size of tissue sample. The second relative configuration corresponds to an operative state that is armed to enable the sampling portion to capture a size of tissue sample. When the sampling portion and handle are in the first relative configuration, the first observation area has a highlighted condition, and when the sampling portion and handle are in the second relative configuration, the second observation area has a highlighted condition. A "highlight" or "highlighted condition" indicates making more noticeable, drawing attention, or making stand out compared to adjacent areas or items. In certain embodiments, the first and second observation areas cannot have their respective highlighted conditions at the same time. In examples in which the first observation area is an opening, the highlighted condition of the first observation area can include visibility of a visually contrasting portion of the sampling portion through the opening. The first and second observation areas may be at least one of (a) longitudinally separated from each other, and (b) laterally offset from each other on respective sides of a longitudinal axis of the handle.

Examples include devices having a handle with opening(s) observable by a user and a needle or cannula portion movable with respect to handle. In one operational state, a portion of the cannula (or a slide member associated with it) having a visual contrast is viewable through an opening in the handle, to advise the user of the device's operational state. One contrasting part of the cannula or slide member may be selectively viewable in two windows, each window indicating a respective operative state. Two contrasting parts of the cannula or slide member may be selectively viewable in two openings, or additional openings and/or contrasting portions may be provided for devices capable of multiple throw-lengths.

BRIEF DESCRIPTION OF THE DRAWINGS

FIG. 3A is a top view of a portion of an embodiment as in FIG. 1.

FIG. 3B is a top view of a different embodiment of the portion of FIG. 3A.

FIG. 6A is a top view of a portion of an embodiment as in FIG. 1 in a first (e.g. unarmed) configuration, with an embodiment as in FIG. 3A attached.

FIG. 6B is a top view of a portion of the embodiment of FIG. 1 in a first (e.g. armed) configuration, with an embodiment as in FIG. 3A attached.

DESCRIPTION OF THE ILLUSTRATED EMBODIMENTS

Figure 1:
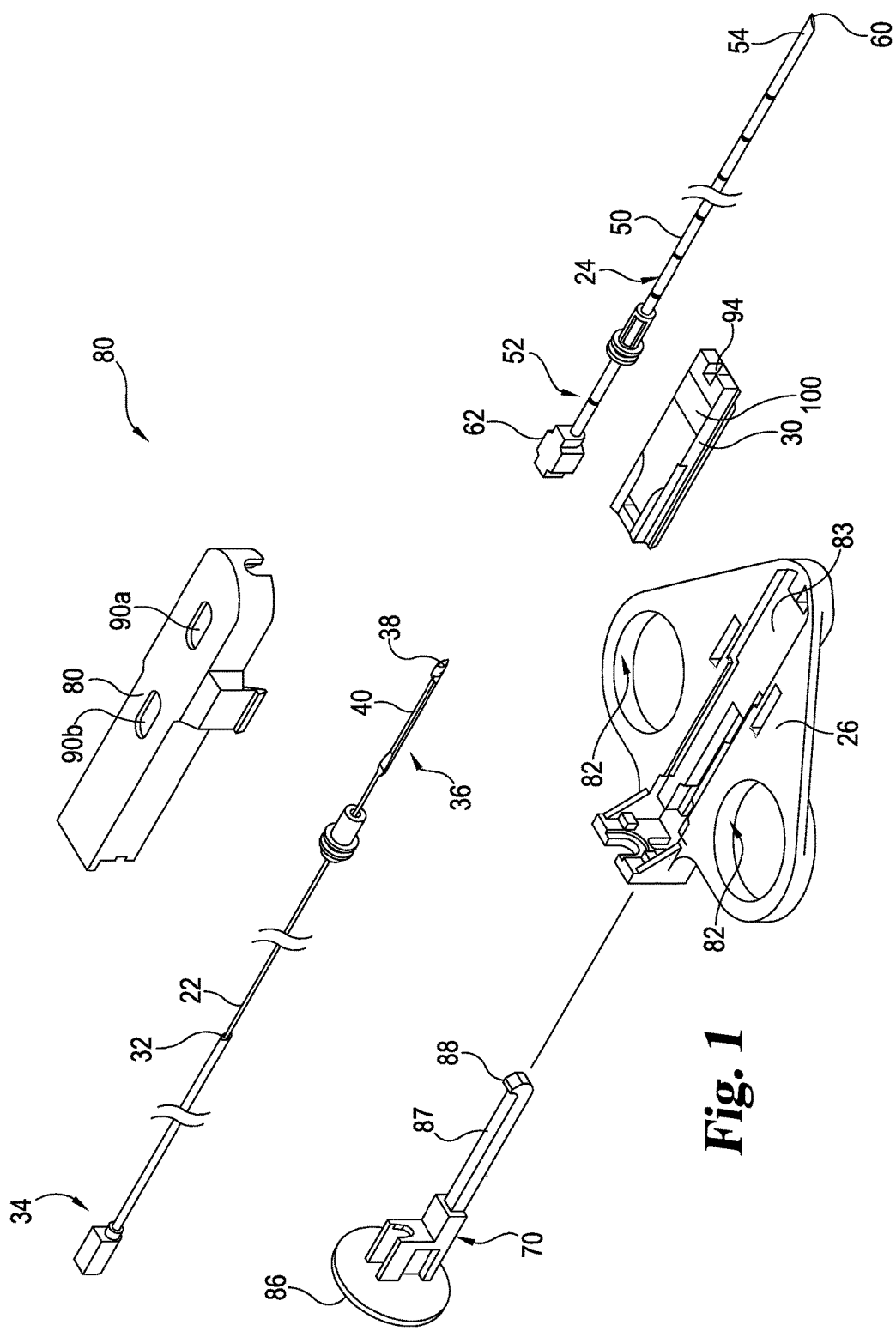
FIG. 1 is an exploded perspective view of parts of an embodiment of a biopsy needle system according to the present disclosure.

For the purposes of promoting an understanding of the principles of the disclosure, reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

Referring now generally to the drawings, there is shown an embodiment of a device for acquiring one or more tissue samples, in the particular form of a biopsy needle 20. Needle 20 includes an inner member or stylet 22, an outer cannula 24 and a handle 26. Stylet 22 is slidable within cannula 24, and both are connected to and operable by handle 26 in this embodiment. Stylet 22 is connected to a slide member 30, which is within and slidable with respect to handle 26 in this embodiment.

Stylet 22 has an elongated body 32 extending between an proximal end 34 and a distal end 36. Elongated body 32 is at least substantially cylindrical in the illustrated embodiment for ease of use and manufacture. Proximal end 34 is connected directly or indirectly to handle 26, for operation during a biopsy procedure as will be further discussed below. Distal end 36 may be sharpened, for example by grinding a surface 38 that is planar and oblique to the longitudinal axis of cannula 22.

Proximal of surface 38 there is formed in stylet 22 a notch or indent 40. Notch 40 is provided so that tissue to be biopsied enters notch 40 and is cut off and contained in notch 40, as further discussed below. As a particular example, notch 40 has a length measured in a longitudinal direction of at least 20 mm, so that in such a case a maximum throw-length for needle 20 is at least 20 mm.

The illustrated embodiment of cannula 24 is tubular, having an elongated body 50 extending between a proximal end 52 and a distal end 54. Proximal end 52 is directly or indirectly connected to handle 26 for operation during the biopsy procedure. Distal end 54 includes a sharpened surface 60. In the illustrated embodiment, an essentially planar oblique section is taken through cannula 24, so that end surface 60 is formed with sharp edges. A hub 62 or other connection is provided on cannula 24 in this embodiment to link cannula 24 to slide member 30.

Handle 26 is connected to and operates each of stylet 22 and cannula 24 so that stylet 22 is within cannula 24, and so that stylet 22 and cannula 24 are slidable with respect to each other. An example of structure usable as part of handle 26 is that currently used with QUICK-CORE® products sold by Cook Medical (Bloomington, Ind.). Embodiments with parts or structures potentially usable in handle 26 are shown in U.S. Provisional Application No. 61/261,857 (filed on Nov. 17, 2009), U.S. application Ser. No. 13/293,162 (filed on Nov. 10, 2011), and U.S. application Ser. No. 13/433,801 (filed on Mar. 29, 2012), the entireties of which are incorporated herein by reference.

Handle 26, in the illustrated embodiment, includes a trigger or actuator 70 connected to slide member 30, and a cover or housing 80. Handle 26 includes finger holds 82 which are substantially circular in this embodiment, and a central track or channel 83 in which slide member 30 is slidable forward and backward (proximally and distally). One or more catches (not shown) are positioned in channel 83 for holding slide member 30 when slide member 30 is pulled sufficiently proximally. Actuator 70 includes a grip or pad 86 positioned at its proximal end in this embodiment, and a distally-extending finger 87 with an end boss 88 that can engage slide member 30 to draw it proximally.

Figure 2:
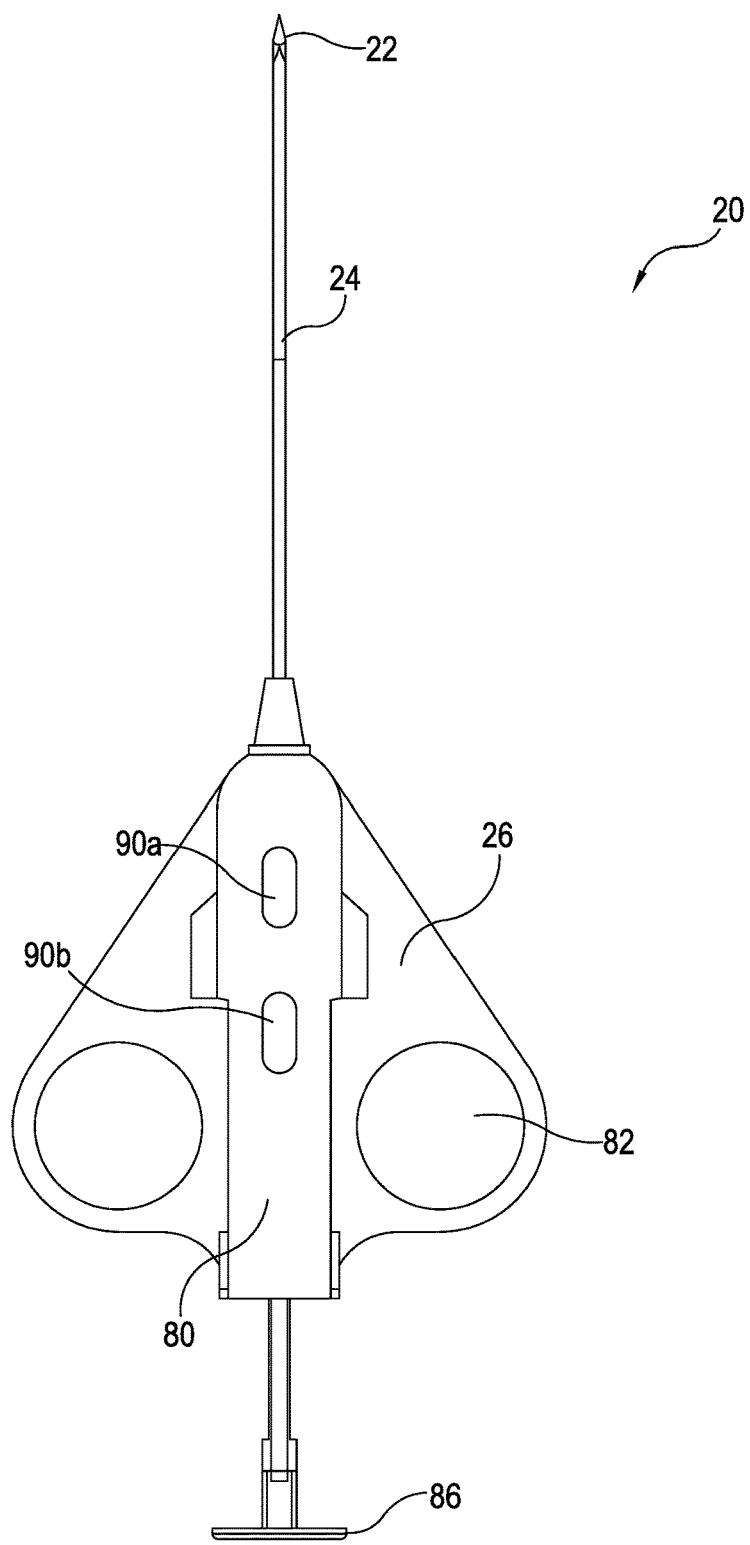
FIG. 2 is a top view of an assembled embodiment as in FIG. 1.
Figure 3C:
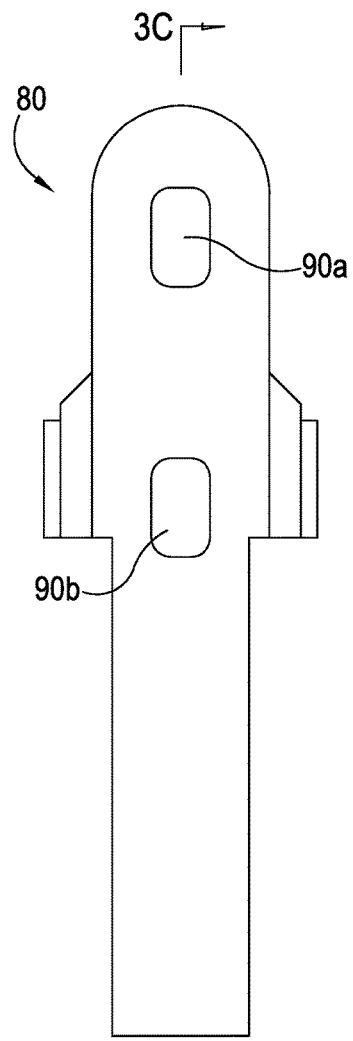
FIG. 3C is a cross-sectional view of the embodiment shown in FIG. 3A.
Figure 3C:
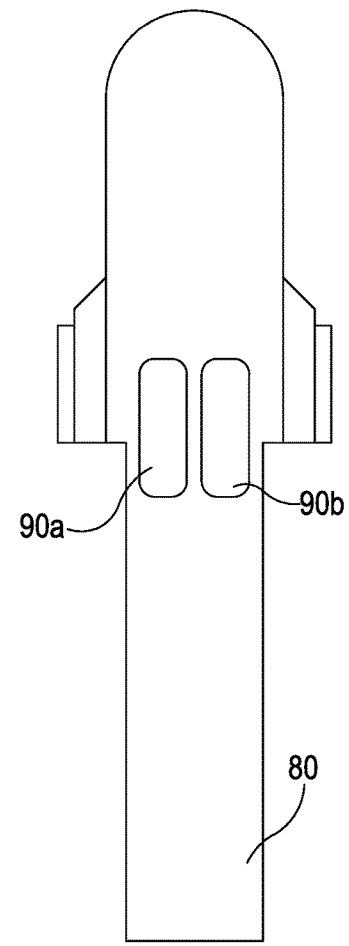
Figure 3C:
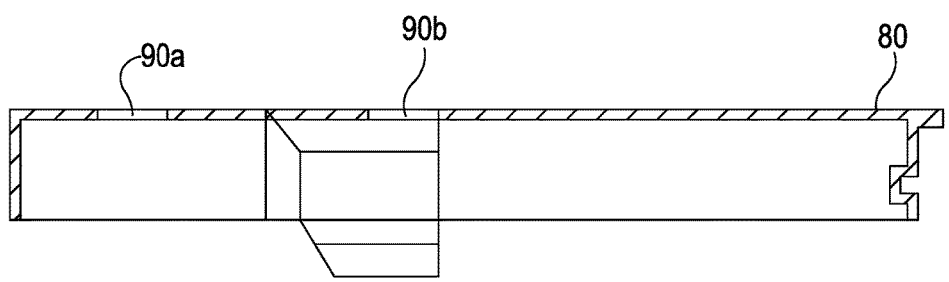

Handle 26 further includes openings 90 in this embodiment, for example two openings 90a, 90b shown in a particular instance through cover 80. Openings 90 are (or are part of) an observation area in handle 26. The term "opening" refers generally to the concept of permitting visualization, and includes uncovered apertures as well as those covered by transparent materials (e.g. a clear plastic window). Openings 90 are large enough for a user to be able to easily see through them and into handle 26, from a distance of at least one to two feet from handle 26. The example of FIGS. 1, 2 and 3A shows openings 90 as being linearly oriented with each other, with their centers on a line that is parallel or along a longitudinal axis of handle 26, and/or on a line that is parallel to the direction of travel of slide member 30. The example of FIG. 3B shows openings 90 that are offset from each other and from a longitudinal axis of handle 26 as viewed from above. A line between the centers of openings 90 in FIG. 3B is substantially perpendicular to a longitudinal axis of handle 26 and the direction of travel of slide member 30. The illustrated embodiments show at least first and second openings 90, and it will be understood that one opening or additional (e.g. three or more) openings may be present in other embodiments. In particular embodiments, respective legends adjacent each opening 90 indicates a particular configuration, as will be further discussed below. Cover 80 fits over channel 83, covering and protecting sliding engagement between slide member 30 and other internal parts of handle 26, e.g. from debris and interference.

Slide member 30 is in the form of a substantially rectangular solid in whole or part in the illustrated embodiment, and is movable within channel 83 of handle 26. Slide member 30 is coupled to a proximal portion of cannula 24, e.g. by inserting hub 62 or other portion of cannula 24 into an opening 94 (which may be complementary to hub 62 or other portion of cannula 24) of slide member 30, with cannula 24 extending from slide member 30. Slide member 30 has an upper surface 96, which as illustrated may be substantially planar throughout and substantially flush with hub 62 when hub 62 is seated in opening 94. When slide member 30 is within channel 83, upper surface 96 faces and is directly under openings 90 through cover 80. In this embodiment, actuator 70 is connected to stylet 22. A spring (not shown) is provided adjacent to slide member 30 to propel slide member 30 and cannula 24 forward, as discussed further below. The spring engages slide member 30 and an internal surface of housing 26.

Figure 4A:
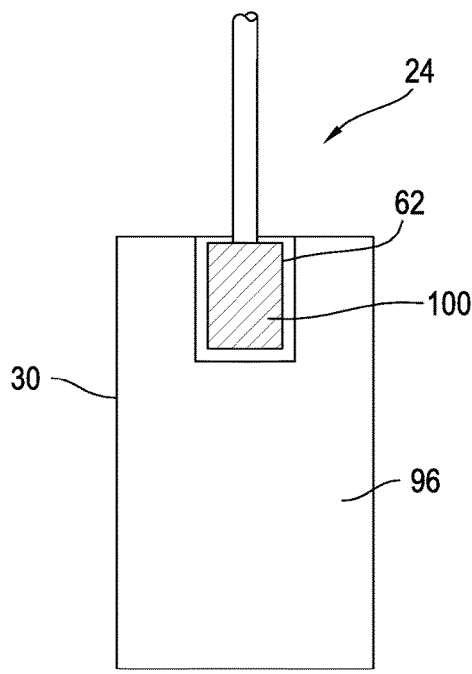
FIG. 4A is a top view of an example of selected portions usable with the embodiment of FIG. 3A.
Figure 4B:
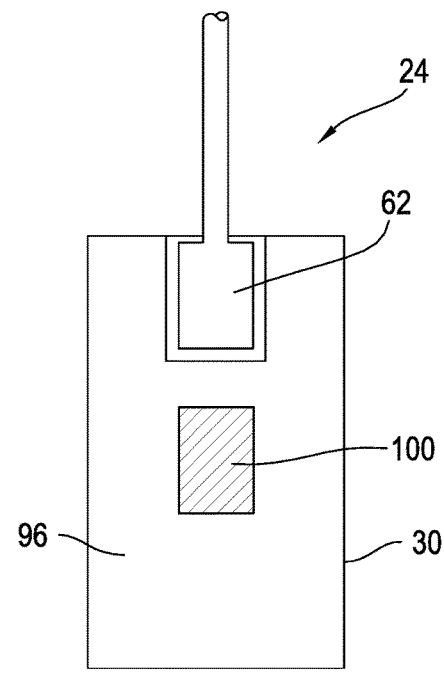
FIG. 4B is a top view of an example of selected portions usable with the embodiment of FIG. 3A.
Figure 4C:
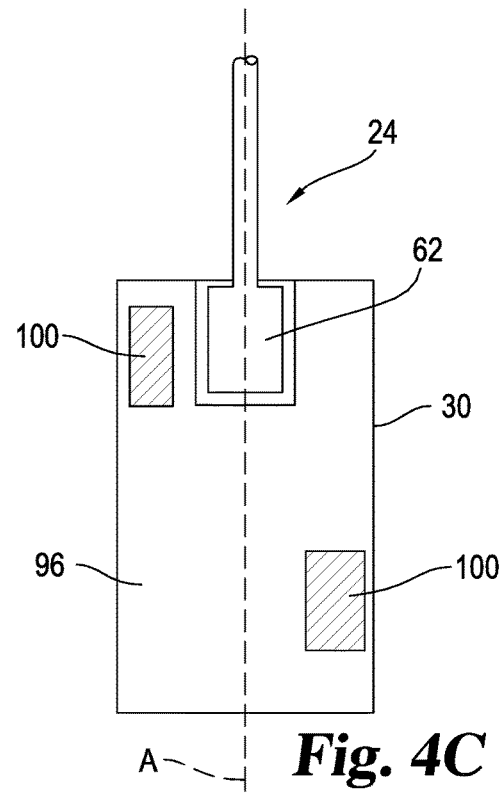
FIG. 4C is a top view of an example of selected portions usable with the embodiment of FIG. 3B.
Figure 5A:
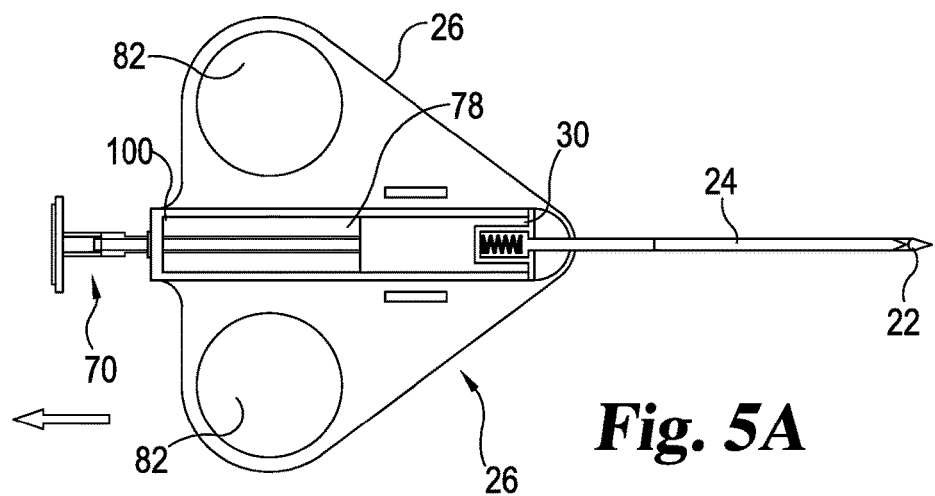
FIG. 5A is a top view of a portion of an embodiment as in FIG. 1 in a first (e.g. unarmed) configuration.
Figure 5B:
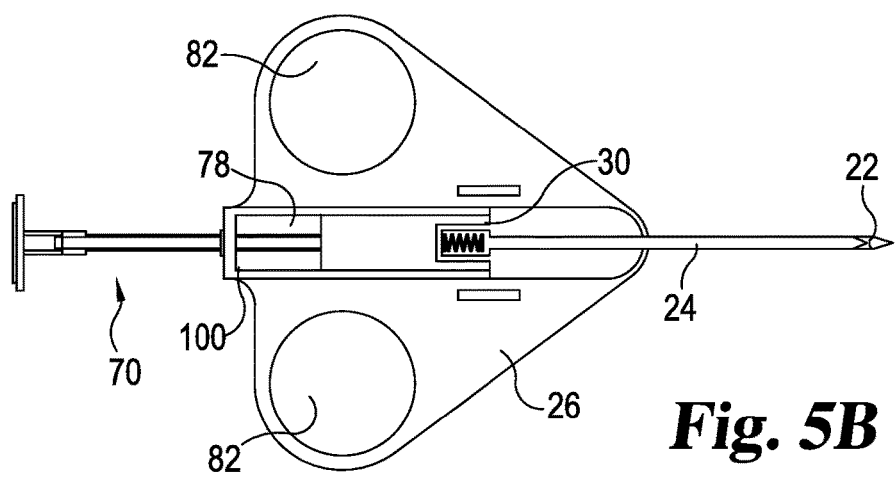
FIG. 5B is a top view of a portion of the embodiment of FIG. 1 in a second (e.g. armed) configuration.

At least one visually contrasting area is provided on or in one or more of the parts that move with respect to handle 26 or parts of it. In the examples of FIGS. 4A and 4B, a visually contrasting section 100 is on a portion of upper surface 96 of slide member 30 and/or on part or all of an exposed portion of hub 62 of cannula 24. The embodiment of FIG. 4A places visually contrasting section 100 on or in hub 62, which is adjacent or surrounded by portions of slide member 30 that are visually similar to handle 26 or portions of it surrounding openings 90. The embodiment of FIG. 4B places visually contrasting section 100 on upper surface 96 of slide member 30, with adjacent or surrounding portions of the surface 96 that are visually similar to each other and to at least part of handle 26 adjacent to or surrounding openings 90. The example of FIG. 4C shows slide member 30 including two separated visually contrasting sections 100, offset from each other longitudinally and offset on either side of a longitudinal axis A of slide member 30. As further explained below, the visually contrasting area(s) 100 and openings 90 are intended to at least partially align at particular configurations of needle 20, e.g. at particular relative locations of slide member 30 with respect to handle 26, so that the user can observe one or more visually contrasting area(s) 100 through one or more opening(s) 90.

By "visually similar" it is meant that the characteristics observable to the eye of a user are very close to or identical to those of other parts, such as the cover 80 and/or other parts of handle 26. For example, if cover 80 is a white or beige color, a lighter neutral color (e.g. white, beige or similar off-white) would be visually similar. By "visually contrasting" it is meant that the characteristics observable to the eye of a user are dissimilar to other parts. Thus, if cover 80 is a white or beige color, visually contrasting colors could include green, red, blue, black and/or others. Further, a visually contrasting area can have or include markings or textures that visually contrast, such as stripes, dots, hatching or other features, particularly where surrounding or adjacent area(s) are of a solid color or have different markings. It will be understood that combinations of color, marking, texture and/or other differences can be used to create visually contrasting areas 100.

Handle 26 is cocked or armed for use by pulling actuator 70 (e.g. via grip 86) backward, i.e. out or away from finger grips 82 and/or the rest of handle 26. With actuator 70 engaging slide member 30, when actuator 70 is pulled, slide member 30 is pulled backward (proximally) within or with respect to handle 26, compressing a spring until a catch engages and holds slide member 30 to maintain an armed or cocked position. Pulling grip 86 proximally moves both cannula 24 and stylet 22 together, maintaining their respective tips at approximately the same location.

In particular embodiments, a needle 20 has a single armed configuration, corresponding to a single throw-length. In such cases, the needle is either armed or unarmed, and the cannula 24 is either fully forward (in the unarmed configuration) or is retracted and held against the force of a compressed spring (in the armed configuration). In the unarmed configuration, a visually contrasting region 100 is visible through a particular opening 90, e.g. the furthest forward opening 90a. Adjacent that furthest forward opening 90a, as suggested above, may be a legend indicating "UNARMED" or similar notation, so that when a visually contrasting region 100 is visible through it, the user will understand that needle 20 is unarmed. In the armed configuration, a visually contrasting region 100 is visible through a different particular opening 90, e.g. the rearward opening 90b. Adjacent that rearward opening 90b, as suggested above, may be a legend indicating "ARMED" or similar notation, so that when a visually contrasting region 100 is visible through it, the user will understand that needle 20 is armed and capable of firing.

In other embodiments, a needle 20 has two or more armed configurations, each corresponding to a particular throw-length. For example, a two throw-length needle may be armable or cockable to a first or intermediate position for a 10 millimeter throw-length, and to a second or farthest position for a 20 millimeter throw-length. In such cases, the needle is either (1) unarmed, (2) armed for the first throw-length, or (3) armed for the second throw-length. In the first armed configuration (for the first throw-length), cannula 24 is retracted against spring force to a first location, and a visually contrasting region 100 is visible through a particular opening 90, e.g. the furthest forward opening 90a. Adjacent that furthest forward opening 90a, as suggested above, may be a legend indicating the first throw-length (e.g. "10 MM" or similar notation), so that when a visually contrasting region 100 is visible through the opening, the user will understand that needle 20 is armed for the first throw-length. In the second armed configuration, a visually contrasting region 100 is visible through a different particular opening 90, e.g. the rearward opening 90b. Adjacent that rearward opening 90b, as suggested above, may be a legend indicating the second throw-length (e.g. "20 MM" or similar notation), so that when a visually contrasting region 100 is visible through it, the user will understand that needle 20 is armed for the second throw-length. In such embodiments, if a visually contrasting region is not visible through either window, it indicates that needle 20 is unarmed. It will be understood that in other embodiments a third opening 90 is placed in a location forward (more proximal) of an opening 90 corresponding to a first (shorter) throw-length, perhaps with an "UNARMED" or similar legend, so that when unarmed a visually contrasting region will be visible through such more-forward opening.

It will further be understood that additional throw-lengths can be provided in a needle 20, with corresponding armed configurations (i.e. relative locations where slide member 30 is held with respect to handle 26) and openings in handle 26. Regardless of the number of throw-lengths provided in a needle, openings and visually contrasting region(s) can be provided so that a region shows through one opening when the needle is in one operational condition (e.g. armed for a particular throw-length, or unarmed), and a region shows through another opening when the needle is in a different operational condition (e.g. armed for another particular throw-length, or simply armed).

Once needle 20 is cocked, the user can perform additional steps in order to fire cannula 24 and obtain a tissue sample. In some embodiments, needle 20 can be primed by moving stylet 22 forward into tissue, exposing notch 40 at least partially beyond the distal end of cannula 24. Needle 20 is fired to capture tissue within notch 40 by releasing spring 78 to move cannula 24 quickly forward over stylet 22 and notch 40. For example, applying force (e.g. through actuator 70) to slide member 30 and/or the catch holding it so as to release or overcome the hold and allow the compressed spring push to slide member 30 and thrust cannula 24 over notch 40 of stylet 22. Thus, in the illustrated embodiment firing the inserted and cocked needle 20 propels cannula 24 over stylet 22, and particularly over notch 40 or the portion of notch 40 that extends from the distal end of cannula 24. The cutting action of cannula 24 via its sharpened distal end 60 during that movement severs and traps tissue within notch 40.

Handle 26 permits the user to be assured and to easily check whether the device is cocked or armed, and/or whether armed for the desired throw-length, when the distal end of the needle is within the patient and so not directly observable. The use of needle 20 will now be described in the context of obtaining a sample of soft tissue for testing purposes. It will be understood that methods for obtaining samples of other tissues or for other purposes are also contemplated.

The surgeon or other medical professional first determines a location in a patient, with its depth under the skin, from which a tissue sample is desired. In one embodiment, stylet 22 and cannula 24 of needle 20 are initially in the above-noted first relative position, e.g. with the distal ends of stylet 22 and cannula 24 substantially co-extant or adjacent. The user considers what length of sample he or she believes is needed. The below-described example concerns a needle providing a choice between two throw lengths, e.g. 10 millimeters (with a first catch position for slide member 30) and 20 millimeters (with a second catch position for slide member 30).

The user cocks needle 20, as noted above, by pulling actuator 70 of handle 26 until slide member 30 catches at the desired position. In the cocked state, in this embodiment, stylet 22 and cannula 24 are in a relative position. Such arming of needle 20 can occur either prior to insertion of needle 20 into the patient, or can occur when the distal end of needle 20 has been inserted to or adjacent to a desired location in the patient.

The user places distal ends 36 and/or 54 of stylet 22 and/or cannula 24 against the skin at a place proximate to the desired location, and inserts needle 20. Needle 20 forces a path through the skin and subcutaneous tissue to a point in or just before the location from which a sample is to be taken. If needle 20 has not previously been cocked or armed for a desired throw-length, then that step can be performed with the distal end of needle 20 inside the patient. Further manipulations to prime or otherwise prepare the needle for firing may be performed.

At any time the user may check to ensure that the needle is armed, and/or if the needle is armed for the desired throw-length. The user can look down to handle 26 and observe openings 90. If the user observes an empty opening (e.g. no part of slide member 30 or hub 62 is visible) or if a visually similar region of slide member 30 and/or hub 62 is visible through an opening, it is an indication to the user that the state indicated by that opening is not the current state of the device. If the user observes an opening through which a visually contrasting region (e.g. of slide member 30 and/or hub 62) is visible, it is an indication to the user that the state indicated by that opening is the current state of the device.

Thus, in a needle 20 having two throw-lengths and separate openings indicating each respective throw-length, the user can immediately tell which throw-length the needle is armed for. If the user observes a visually contrasting region through the opening corresponding to the first throw-length, he or she knows the needle is armed for the first-throw length. A visually similar region or an empty space may be visible in the other opening. If a visually similar region or an empty space is visible in both openings, it is an indication that the needle is unarmed. As another example, in a needle having one armed condition, and respective openings indicating an armed and unarmed condition are provided, in the armed condition a visually contrasting region will be visible through the opening corresponding to the armed condition. A visually similar or empty space may be visible through the opening corresponding to the unarmed condition. Conversely, in the unarmed condition a visually contrasting region will be visible through the opening corresponding to the unarmed condition, and a visually similar or empty space may be visible through the opening corresponding to the armed condition. The user need not see the distal end of needle 20 in order to determine whether it is armed as he or she desires.

Having verified that needle 20 is in the desired armed condition, the user releases the hold on slide member 30, as indicated above, to fire cannula 24 forward. Slide member 30 moves forward from its armed or cocked position to its unarmed or rest position (e.g. as far forward as handle 26 will allow). The cutting action of cannula 24 severs the sample of tissue within notch 40. Tissue outside notch 40, either radially or longitudinally, is not trapped in notch 40 between cannula 24 and stylet 22.

After firing, needle 20 is withdrawn from the patient. Once needle 20 is withdrawn, the tissue sample is removed by cocking and priming needle 20, as indicated above, to expose notch 40 and the tissue within it. The tissue sample can be extracted from notch 40 using a forceps or other tool, or in some embodiments by inverting notch 40 and allowing the tissue to drop out of notch 40 into a specimen dish or other container. If the user determines that additional sample(s) are needed, then the procedure above can be repeated to obtain such samples.

While an illustration of needle 20 discussed above has two throw-length settings, exemplified as 10 millimeters and 20 millimeters, it will be understood that other throw lengths can be used in place of one or both of such lengths. Further, as noted previously it will be understood that three or more throw-length settings may be provided in a needle system or kit, by providing three or more catches each holding slide member 30 at respective different positions with respect to handle 26. As one example, a system or kit may be provided having sterilized parts including a needle 20 with a largest throw-length of 20 millimeters, and two smaller, intermediate lengths, such as 15 and 10 millimeters.

As used herein, the term "throw length" is intended to indicate a measurement of the length of a tissue sample obtained and/or the distance a part is moved forward in use of the device. For example, a 20 millimeter throw length for the embodiments noted above indicates that stylet 22 is advanced in the priming step so that approximately 20 millimeters of notch 40 (or the entire notch 40 if its length is 20 millimeters, in this example) is exposed from cannula 24.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected. It is to be understood that features described with respect to one embodiment or aspect of the disclosure can be used with other embodiments or aspects of the disclosure.

What is claimed is:

1. A tissue sample acquisition device, comprising:
  a handle, the handle having a surface with first and second openings and an actuator that moves linearly proximally and distally with respect to the surface;
  a sampling portion having an elongated cannula at least partially extending from the handle connected to a slide member adapted to slide with respect to the surface, the sampling portion having at least one visually contrasting portion, the at least one visually contrasting portion having an immediately observable visual contrast with one or more adjacent parts of the handle;
  wherein at least part of the sampling portion and the handle are movable with respect to each other between at least a first relative configuration and a second relative configuration, the first relative configuration corresponding to a first armed state operationally adapted to result in obtaining a first sample size, and the second relative configuration corresponding to a second armed state operationally adapted to result in obtaining a second sample size different from the first sample size, and wherein when the sampling portion and handle are in the first relative configuration, at least part of the at least one visually contrasting portion is visible through the first opening, and when the sampling portion and handle are in the second relative configuration, at least part of the at least one visually contrasting portion is visible through the second opening,
  wherein pulling the actuator linearly with respect to the handle surface a first distance from a rest position produces the first relative configuration, and pulling the actuator linearly with respect to the handle surface a second distance from a rest position produces the second relative configuration.

2. The device of claim 1, wherein in the first relative configuration, a different view is visible through the second opening, the different view comprising one of (a) a part of the sampling portion visually similar to an area adjacent the second opening and (b) empty space.

3. The device of claim 1, wherein in the second relative configuration, a different view is visible through the first opening, the different view comprising one of (a) a part of the sampling portion visually similar to an area adjacent the second opening and (b) empty space.

4. The device of claim 1, further comprising a spring within the handle to propel at least a portion of the slide member in translation.

5. The device of claim 1, further comprising an elongated stylet at least partially within the cannula, the stylet having a distal notch whereby tissue can enter the notch and be cut off and contained in the notch by translational travel of the cannula.

6. The device of claim 5, wherein the slide member is adapted to be propelled translationally to move the cannula over the notch.

7. The device of claim 1, wherein the at least one visually contrasting portion is at least part of the slide member.

8. The device of claim 1, wherein the slide member is of the same color as the handle except for a portion of a color visually contrasting with the slide member.

9. The device of claim 1, wherein the handle has a longitudinal axis generally parallel to a portion of the elongated cannula adjacent to or within the handle, and wherein a line connecting the first and second openings is generally parallel to the longitudinal axis.

10. The device of claim 1, wherein the first relative configuration is a relative position between the slide member and the surface wherein the slide member is held at rest relative to the surface, and the second relative configuration is a relative position between the slide member and the surface wherein the slide member has been retracted from the first relative configuration and is held at rest relative to the surface.

11. The device of claim 1, wherein the visually contrasting portion is a portion of an upper surface of the slide member that does not extend through the handle.

12. The device of claim 1, wherein the at least one visually contrasting portion is not visible through the first and second openings at the same time.

* * * * *